(12) United States Patent
Lin (10) Patent No.: US 12,383,151 B2
(45) Date of Patent: Aug. 12, 2025

(54) ARM BAND ACCESSORY

(71) Applicant: HEALTH & LIFE CO., LTD., New Taipei (TW)

(72) Inventor: Chia-Chien Lin, New Taipei (TW)

(73) Assignee: HEALTH & LIFE CO., LTD., New Taipei (TW)

( * ) Notice: Subject to any disclaimer, the term of this patent is extended or adjusted under 35 U.S.C. 154(b) by 698 days.

(21) Appl. No.: 17/738,832

(22) Filed: May 6, 2022

(65) Prior Publication Data

US 2023/0263415 A1    Aug. 24, 2023

(30) Foreign Application Priority Data

Feb. 23, 2022   (TW) ................................ 111201869

(51) Int. Cl.
| | | |
|---|---|---|
| *A61B 5/022* | (2006.01) | |
| *A61B 5/00* | (2006.01) | |
| *A61B 5/256* | (2021.01) | |

(52) U.S. Cl.
CPC .......... *A61B 5/02233* (2013.01); *A61B 5/256* (2021.01); *A61B 5/6831* (2013.01)

(58) Field of Classification Search
CPC . A61B 5/02233; A61B 5/6831; A61B 5/6843; A61B 5/6824; A61B 5/681; A61B 5/6838; A61B 5/022–02241; B29C 66/1122; Y10S 24/906; A44C 5/246
See application file for complete search history.

(56) References Cited

U.S. PATENT DOCUMENTS

| | | | |
|---|---|---|---|
| 2013/0165803 A1* | 6/2013 | Hung | A61B 5/02233 600/499 |
| 2015/0173633 A1* | 6/2015 | Shimizu | A61B 5/02427 600/479 |
| 2018/0192947 A1* | 7/2018 | Tokko | B29C 66/1122 |
| 2020/0214578 A1* | 7/2020 | Zhang | A61B 5/02125 |
| 2023/0000372 A1* | 1/2023 | Harada | A61B 5/681 |
| 2023/0038858 A1* | 2/2023 | Kuo | A61B 5/02233 |

\* cited by examiner

*Primary Examiner* — Eric F Winakur
*Assistant Examiner* — Noah M Healy
(74) *Attorney, Agent, or Firm* — HSML P.C.

(57) ABSTRACT

An arm band accessory includes a band cuff, a linking unit, and a connecting unit. The linking unit includes a securing member, a rotatable member, and an operating mechanism. The securing member is mounted to the band cuff. The rotatable member is pivotally connected to the securing member and the operating mechanism. A first end section of the band cuff is operable to extend through the connecting unit and be folded back to form a first constrained space with the band cuff, the linking unit and the connecting unit when the operating mechanism is in a fixed state, and to form a second constrained space with the band cuff, the linking unit and the connecting unit when the operating mechanism is in a unfolded state.

9 Claims, 7 Drawing Sheets

ARM BAND ACCESSORY

CROSS-REFERENCE TO RELATED APPLICATION

This application claims priority to Taiwanese Utility Model Patent Application No. 111201869, filed on Feb. 23, 2022.

FIELD

This disclosure relates to an arm band accessory, specifically to an arm band accessory that can be adjusted based on the arm circumference.

BACKGROUND

Generally, in a blood pressure meter that is easy to move and store, the arm band accessory often used is an elongated strap that is fastened by a set of male and female adhesive fasteners (Hook-and-loop fasteners), and using different positions of contact between the male adhesive fastener and the female adhesive fastener, a fit that can be adjusted to different arm circumferences can be achieved.

When measuring blood pressure, the tightness of the arm band accessory around the arm needs to retain a gap of about two fingers, an overly loose or overly tight fit will affect the accuracy of the measured blood pressure value. To accurately measure the blood pressure value, someone other than the test subject is required to assist the subject to fit the arm band accessory correctly on an arm of the subject. Also, after each measurement, the arm band accessory must be loosened so that the arm band accessory can be detached. However, the arm band accessory is not easy to operate when used alone, i.e., adjusting the arm band accessory to an appropriate fit size to obtain accurate measurement results, particularly for the elderly who live alone.

SUMMARY

Therefore, an objective of the present disclosure is to provide an arm band accessory that is convenient to operate with one hand.

According to the disclosure, the arm band accessory includes a band cuff, a linking unit, and a connecting unit.

The band cuff includes a cuff body that extends in a longitudinal direction, a first fastening portion, and at least one second fastening portion. The cuff body has a first surface and a second surface that are opposite to each other, and a first end section and a second end section that are opposite to each other in the longitudinal direction. Two ends of each of the first surface and the second surface are respectively located at the first end section and the second end section of the cuff body. The first fastening portion and the at least one second fastening portion are disposed on the first surface. The at least one second fastening portion is operable to be detachably fastened to the first fastening portion.

The linking unit includes a securing member, a rotatable member, and an operating mechanism. The securing member is mounted to the cuff body and proximate to the second end section. The rotatable member is pivotally connected to the securing member and the operating mechanism. The operating mechanism is operable to convert between a fixed state, where the operating mechanism is stacked on the rotatable member and is detachably fixed to the securing member, and an unfolded state, where the operating mechanism is away from the securing member and where the operating mechanism and the rotatable member are unfolded. The connecting unit includes a connecting belt and a connecting ring. The connecting belt has opposite ends that are respectively connected to the operating mechanism and the connecting ring. The first end section is operable to extend through the connecting ring and be folded back to attach the at least one second fastening portion to the first fastening portion to form a first constrained space with the band cuff, the linking unit and the connecting unit when the operating mechanism is in the fixed state, and to form a second constrained space with the band cuff, the linking unit and the connecting unit when the operating mechanism is in the unfolded state. The second constrained space is larger than the first constrained space.

BRIEF DESCRIPTION OF THE DRAWINGS

Other features and effects related to the present disclosure will be clearly presented in the embodying manner with reference to the drawings, in which.

DETAILED DESCRIPTION

Figure 1:
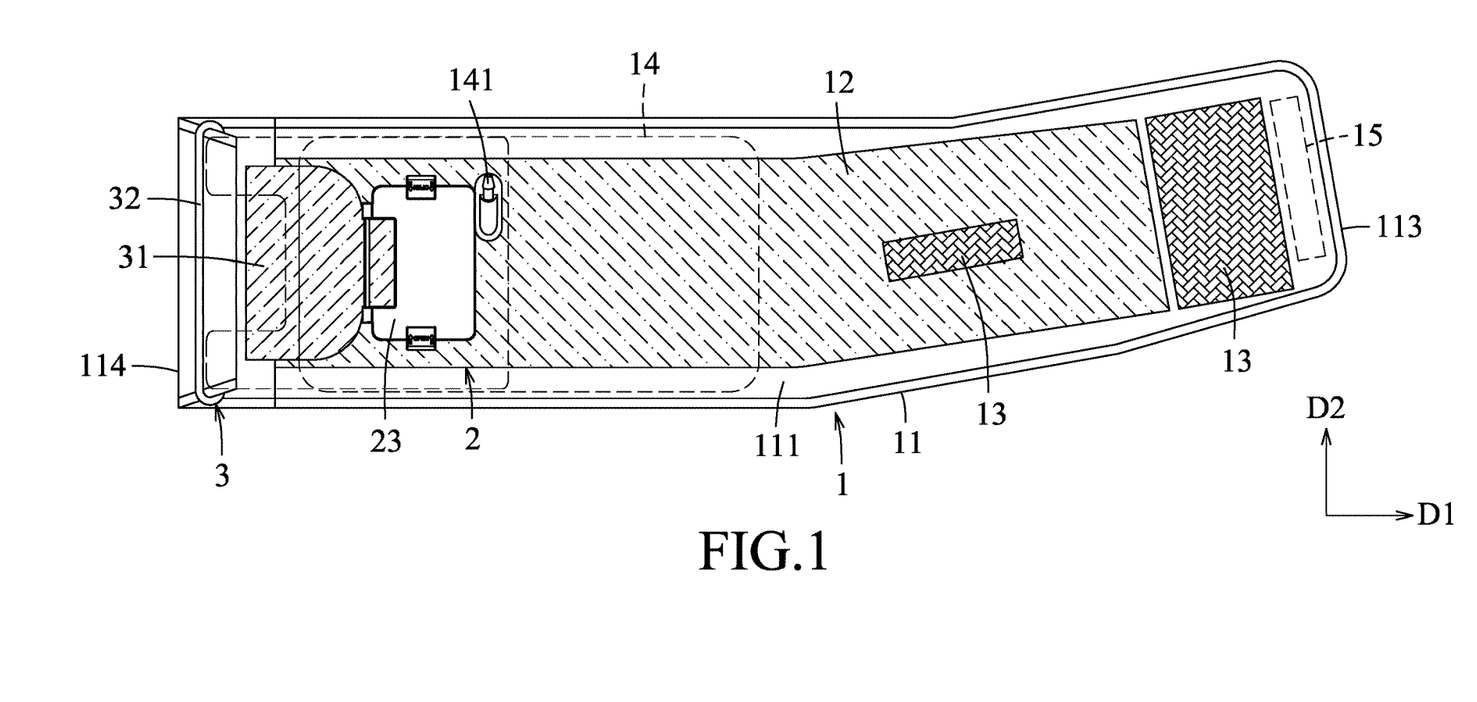
FIG. 1 is a schematic view of an embodiment according to the present disclosure in an unfolded state.
Figure 2:
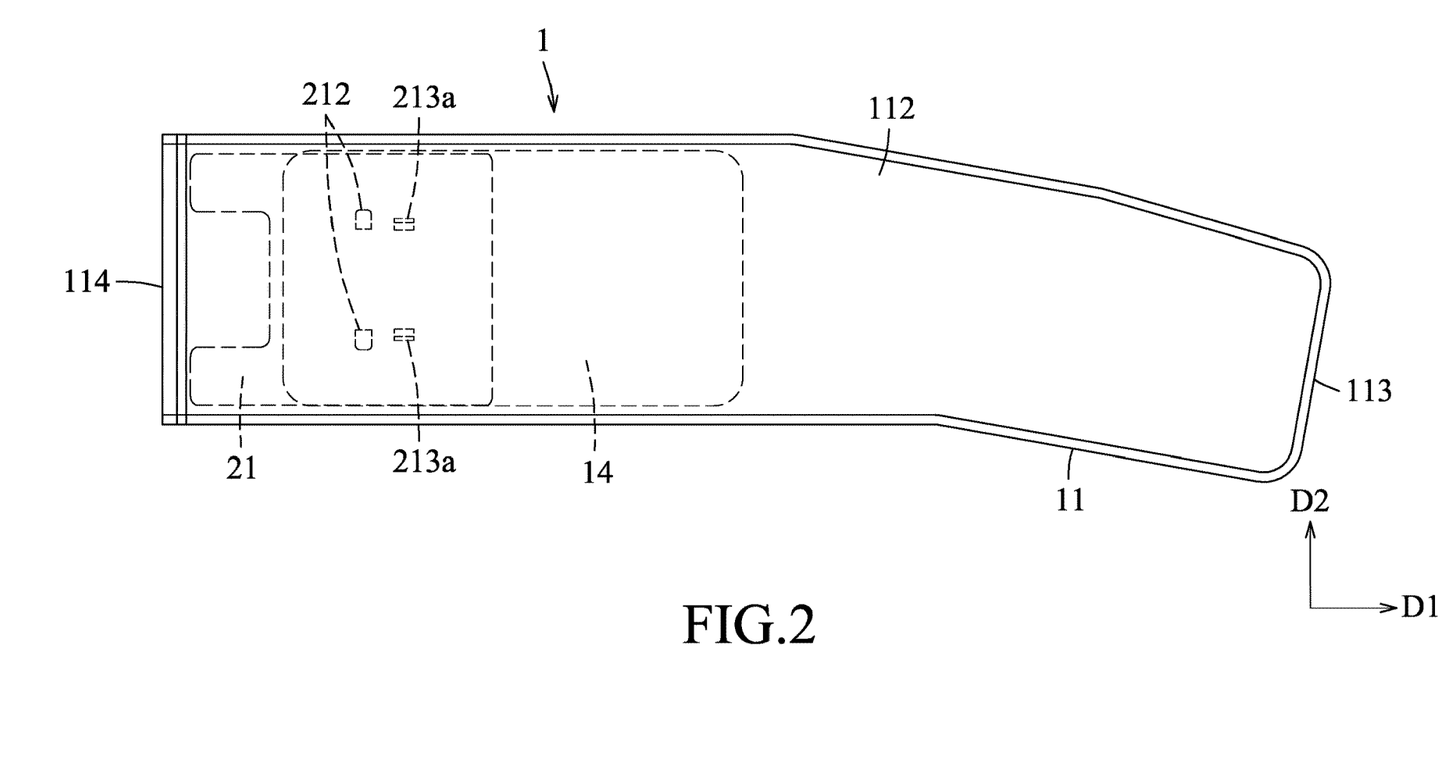
FIG. 2 is another schematic view of the embodiment in the unfolded state.
Figure 3:
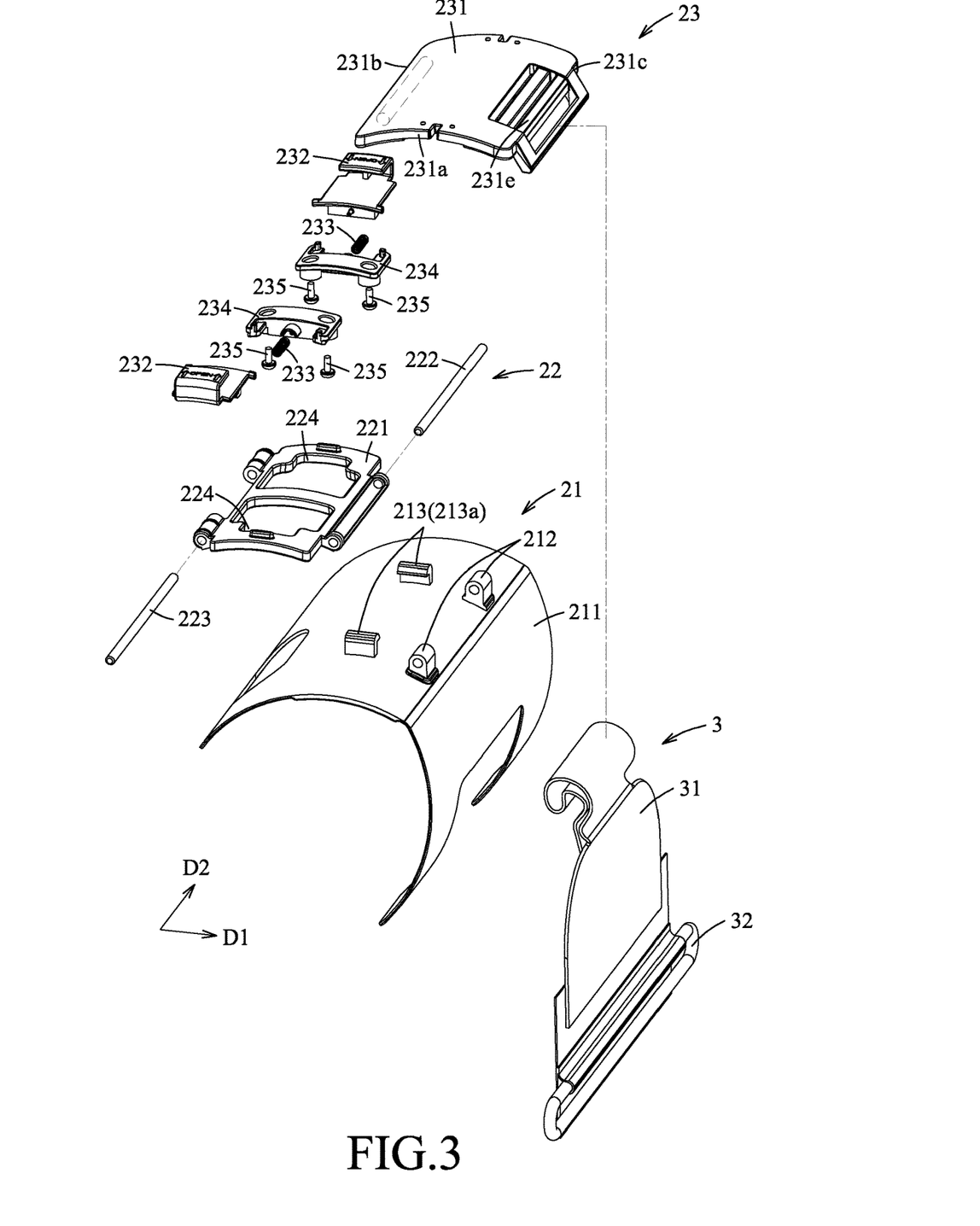
FIG. 3 is an exploded perspective view of a linking unit and a connecting unit of the embodiment.

Referring to FIGS. 1 to 3, an embodiment of an arm band accessory according to the present disclosure is adapted to be connected to a measurement module (not shown) of a blood pressure meter for measuring a blood pressure value. The arm band accessory includes a cuff 1, a linking unit 2, and a connecting unit 3.

The cuff (1) includes a cuff body 11 extending in a longitudinal direction (D1), a first fastening portion 12, two second fastening portions 13, an inflatable bladder 14 and a magnet member (15). The cuff body 11 has a first surface 111 and a second surface 112 opposite to each other, and a first end section 113 and a second end section 114 opposite to each other in the longitudinal direction (D1). Two ends of each of the first surface 111 and the second surface 112 are respectively located at the first end section 113 and the second end section 114 of the cuff body 11. The first fastening portion 12 and the second fastening portions 13 are disposed on the first surface 111. In this embodiment, the first fastening portion 12 is a female fastener covered with a ring structure, the second fastening portion 13 is a male fastener covered with a hook structure, and the first and second fastening portions 12, 13 are configured as a hook-and-loop mechanism. The second fastening portion 13 is operably to be detachably fastened to the first fastening portion 12. The first fastening portion 12 extends in the longitudinal direction (D1) to be strip-shaped and covers a majority of the area of the first surface 111. One of the second fastening portions 13 is located between the first fastening portion 12 and the first end section 113 and is close to the first end section 113, and the other of the second fastening portions 13 is located in the first fastening portion 12 and extends in the longitudinal direction D1. The inflatable bladder 14 is disposed inside the cuff body 11 and in proximity to the second end section 114, and has a nozzle 141 for charging and discharging gas. The magnet member 15 is disposed on the strap cuff body 11 and is adjacent to the first end section 113.

Referring to FIGS. 1 and 3 to 5, the linking unit 2 includes a securing member 21, a rotatable member 22, and an operating mechanism 23.

The securing member 21 is disposed in the cuff body 11 and proximate to the second end section 114, and has a base body 211 that is bent and flexibly expandable, a first pivot portion 212 that is connected to the base body 211 and that protrudes out of the first surface 111 for pivotal connection with the rotatable member 22, and an engaging portion 213 that is connected to the base body 211 and that protrudes out of the first surface 111 for engagement with the operating mechanism 23. The base body 211 is partially overlapped with the inflatable bladder 14, can be flexibly expanded to be suitable for wearers of different arm circumferences, and can be positioned on the arm of the wearer so that the inflatable bladder 14 can be positioned in place of the wearer's arm while mitigating the interference of the cuff 1 to the wearer's arm, thereby making signal feedback more accurate when measuring blood pressure. The engaging portion 213 is farther away from the second end section 114 than the first pivot portion 212. In this embodiment, the engaging portion (213) includes two engaging hooks 213a are spaced apart from each other in a width direction (D2) perpendicular to the longitudinal direction (D1), and ends of the engaging hooks 213a bend and extend toward each other.

Figure 4:
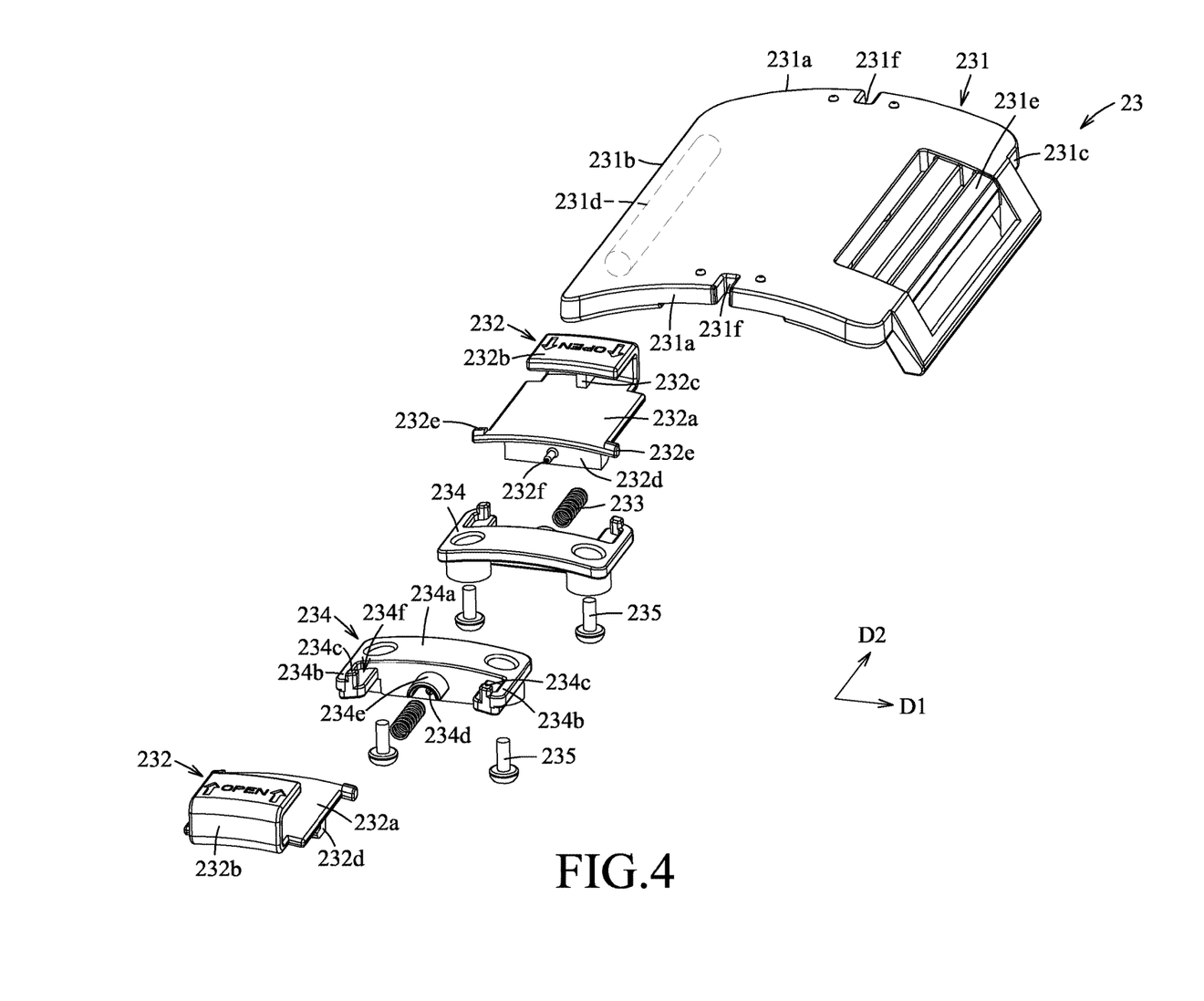
FIG. 4 is an enlarged fragmentary area of FIG. 3.

The rotatable member 22 is pivotally connected to the securing member 21 and the operating mechanism 23. In this embodiment, the rotatable member 22 has a main body 221, a first pivot rod 222 that is connected to an end of the main body 221, that extends in the width direction (D2) and that is connected pivotally to the first pivot portion 212, and a second pivot rod 223 that is connected to another end of the main body 221 opposite to the first pivot rod 222. The main body 221 has two openings 224 to permit the engaging hooks 213a to pass therethrough.

The operating mechanism 23 includes a main member 231, two pressing members 232, two resilient members 233, and two limit members 234.

The main member 231 includes two first edges 231a that are parallel to the longitudinal direction (D1) and that are opposite to each other, a second edge 231b and a third edge 231c that are parallel to the width direction D2 and that are connected to the first edges 231a, a second pivot portion 231d that is proximate to the second edge 231b and that is pivotally connected to the second pivot rod 223, a connecting portion 231e that is proximate to the third edge 231c, and two limit notches 231f that are recessed inwardly and respectively from the first edges 231a and that are parallel to the width direction (D2).

The limit members 234 are mounted fixedly to an inner surface of the main member 231 facing the cuff body 11, are respectively disposed corresponding to the pressing members 232, and cooperate with the main member 231 to hold the pressing members 232.

Each limit member 234 has a securing portion 234a fixed to the main member 231, two arm portions 234b extending from the securing portion 234a and parallel to the width direction (D2), two stop blocks 234c respectively located on ends of the arm portions 234b, a first positioning protrusion 234d extending from the securing portion 234a parallel to the width direction (D2) and located between the arm portions 234b, and a limit arc piece 234e extending from the securing portion 234a and semi-curvedly surrounding the first positioning protrusion 234d. The arm portions 234b and the securing portion 234a cooperatively define a guide groove 234f, and the first positioning protrusion 234d and the limiting arc piece 234e are located below the guide groove 234f.

In this embodiment, each limit member 234 is fixed to the main member 231 by using two locking members 235.

The pressing members 232 are arranged on the main member 231 arranged in the width direction D2, and are movable between a fastening position, where the pressing members 232 respectively engage with the engaging hooks 213a, and a releasing position, where the pressing members 232 are respectively disengaged from the engaging hooks 213a.

Specifically, the pressing members 232 are respectively located at the first edges 231a and are movable parallel to the width direction (D2). The limit notches 231f correspond respectively in position to the pressing members 232.

The pressing members 232 are moved toward each other when moved from the fastening position to the releasing position.

Each pressing member 232 has a support portion 232a abutting against the inner surface of the main member 231, a U-shaped press portion 232b extending from the support portion 232a and accommodating a respective one of the first edges 231a, a limit block 232c connected to the press portion 232b and slidable parallel to the width direction (D2) within a respective limit notch 231f, an engaging segment 232d extending from the support portion 232a away from the main member 231 for engaging with the respective engaging hook 213a, two guide blocks 232e extending respectively from two opposite sides of the support portion 232a parallel to the longitudinal direction (D1), and a second positioning protrusion 232f extending from the engaging segment 232d parallel to the width direction (D2) toward the first positioning protrusion 234d of the respective one of the limit members 234.

The guide blocks 232e abut respectively against the arm portions 234b and are slidable parallel to the width direction (D2) within the guide groove 234f. When the pressing members 232 are disposed at the fastening position, the guide blocks 232e of each pressing member 232 are respectively stopped by the stop blocks 234c of the respective one of said limit members 234 so as to prevent separation of the pressing member 232 from the main member 231. Each of the resilient members 233 is located between a respective one of the pressing members 232 and a respective one of the limit members 234.

In this embodiment, each of the resilient members 233 is a compression spring, and has two ends sleeved respectively on the first positioning protrusion 234d of the respective one of the limit members 234 and the second positioning protrusion 232f of the respective one of the pressing members 232 and respectively abutting against the securing portion 234a of the respective one of the limit members 234 and the engaging segment 232d of the respective one of the pressing members 232.

The resilient members 233 are disposed respectively corresponding to the pressing members 232 to provide a restoring force for restoring the pressing members 232 to the fastening position. The pressing members 232 press the resilient members 233 when moved from the fastening position to the releasing position so as to maintain the resilient members 233 to be compressed and store a resilient restoring force. With the pressing force to the pressing members 232 being deactivated, the pressing members 232 are restored to the fastening position by the resilient members 233. When the resilient members 233 are compressed, the limit arc pieces 234e support the resilient members 233 so as to keep the resilient members 233 linearly compressed.

The operating mechanism 23 is operable between a fixed state (see FIG. 1), where the operating mechanism 23 is stacked on the rotatable member 22 and is detachably fixed to the securing member 21, and an unfolded state (see FIG. 5), where the operating mechanism is away from the securing member 21 and where the operating mechanism 23 and the rotatable member 22 are unfolded.

Specifically, when the operating mechanism 23 is in the fixed state, the engaging segments 232d of the pressing members 232 are engaged respectively with the engaging hooks 213a, the rotatable member 22 is located between the main member 231 and the securing member 21, and the third edge 231c of the main member 231 is adjacent to the first pivot rod 222.

Figure 5:
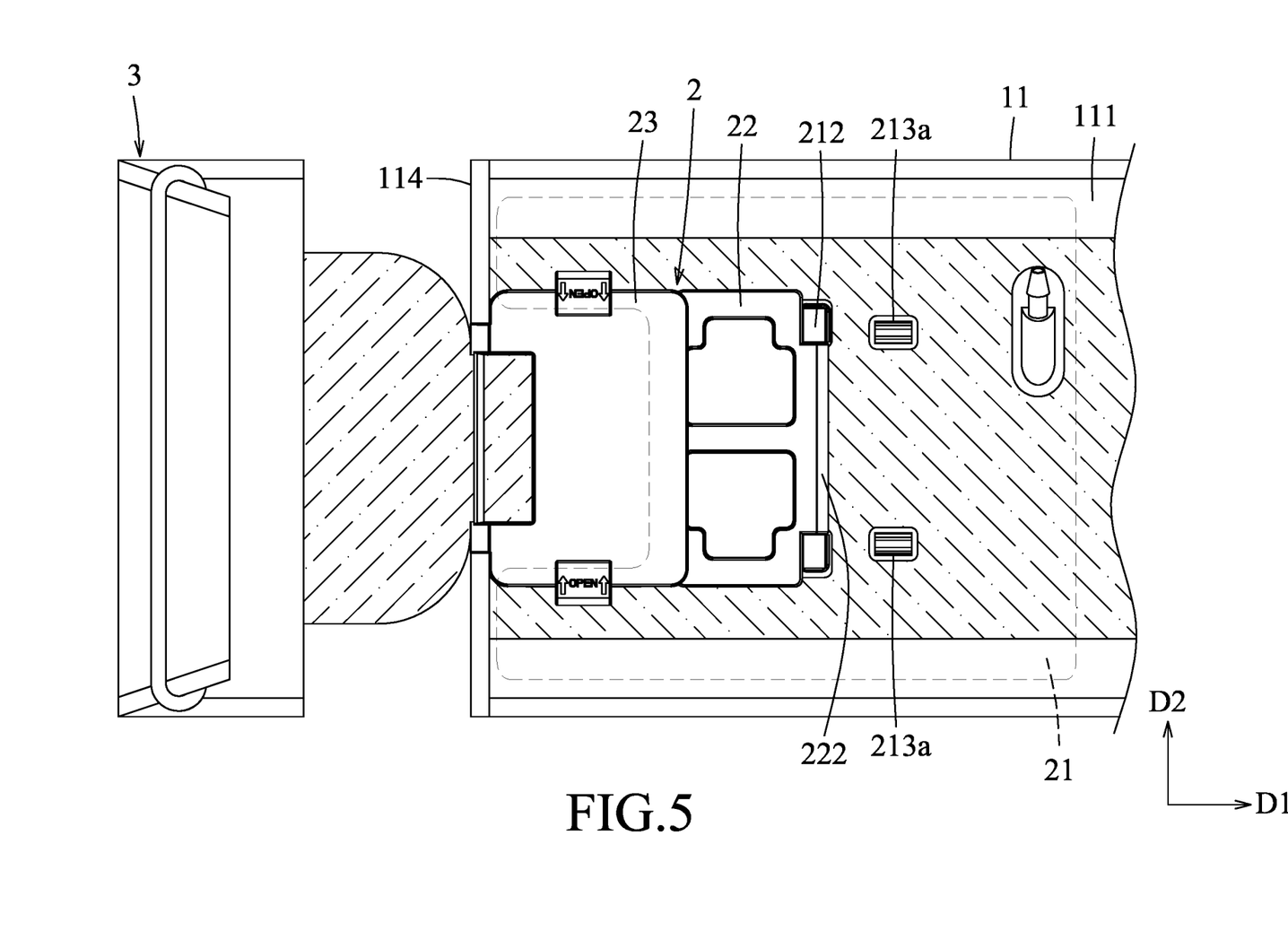
FIG. 5 is a fragmentary schematic view of the linking unit in the unfolded state.

To switch the operating mechanism 23 from the fixed state to the unfolded state, the wearer can operate with one hand by using the thumb and the index finger to respectively press the pressing members 232, so that the pressing members 232 move toward each other to thereby move from the engaging position to the releasing position and detach the engaging segments 232d from the engaging hooks 213a. At the same time, the wearer pulls the operating mechanism 23 to drive the main member 231 to pivot relative to the rotatable member 22 about the second pivot rod 223 as an axis, and to drive the rotatable member 22 to pivot relative to the securing member 21 about the first pivot rod 222 as an axis. As such, the rotatable member 22 is turned about 180 degrees to unfold the operating mechanism 23 and the rotatable member 22 toward the second end section 114 such that the operating mechanism 23 is converted to the unfolded state.

When the pressing members 232 are pressed the resilient members 233 are compressed, and restoring force accumulates in the resilient members 233. When the wearer releases the pressing members 232, the pressing members 232 are restored to the fastening position by the accumulated restoring force of the resilient members 233.

When the wearer wants to secure the operating mechanism 23 and the securing member 21 (i.e., to return the operating mechanism 23 to the fixed state), the wearer simply rotates back the rotatable member 22 to its original position and then presses the main member 231 toward the securing member 21, the engaging segments 232d of the pressing members 232 can be deformed resiliently relative to the engaging hooks 213a and then engage once again with the engaging hooks 213a.

Referring to FIGS. 1, 3, 6 and 7, the connecting unit 3 includes a connecting belt 31 and a connecting ring 32.

The connecting belt 31 has opposite ends that are respectively connected to the operating mechanism 23 and the connecting ring 32. Specifically, the main member 231 is connected between the rotatable member 22 and the connecting belt 31.

In this embodiment, the connecting portion 231e of the main member 231 is formed with three cross bars and three through slots arranged in a staggered manner, and the connecting belt 31 is extended through the through slots and is sewn to be secured to the connecting ring 32.

Figure 6:
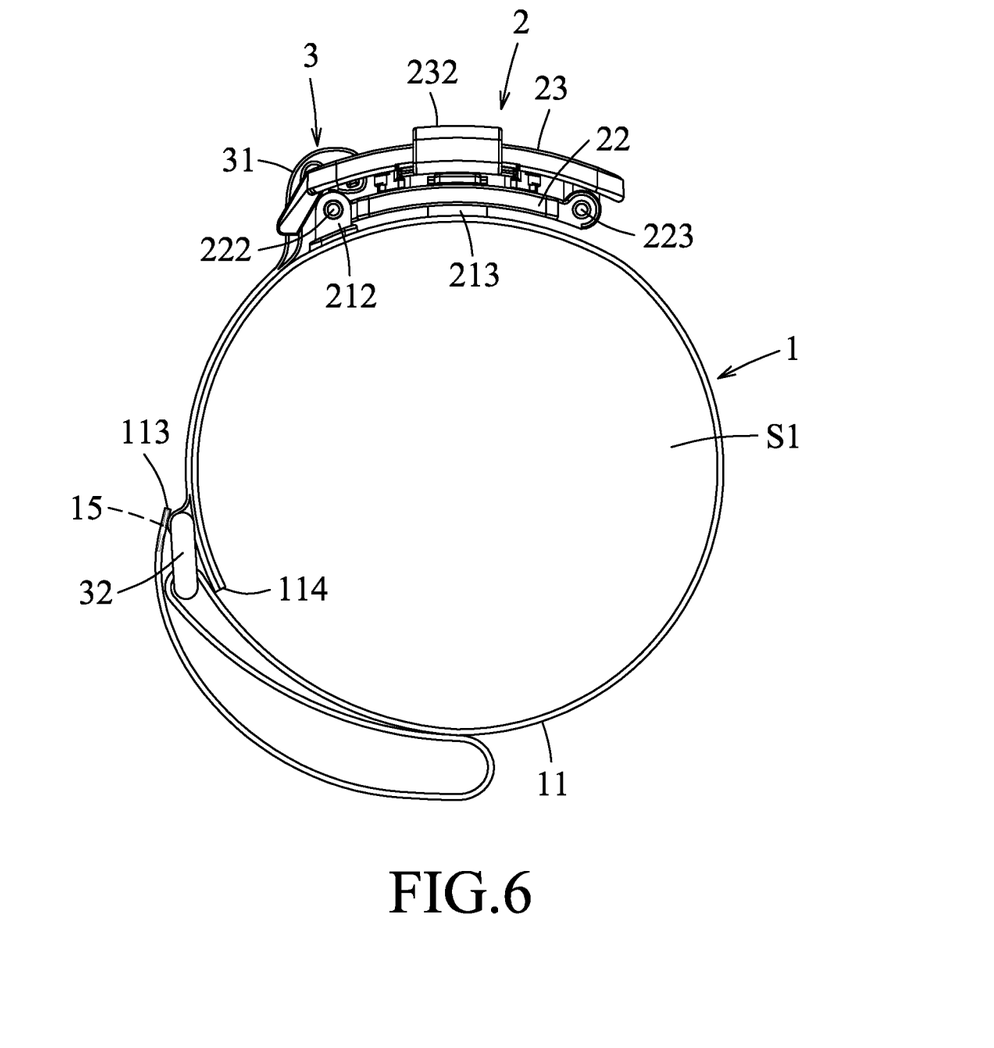
FIG. 6 is a side schematic view of the embodiment forming a first constrained space.
Figure 7:
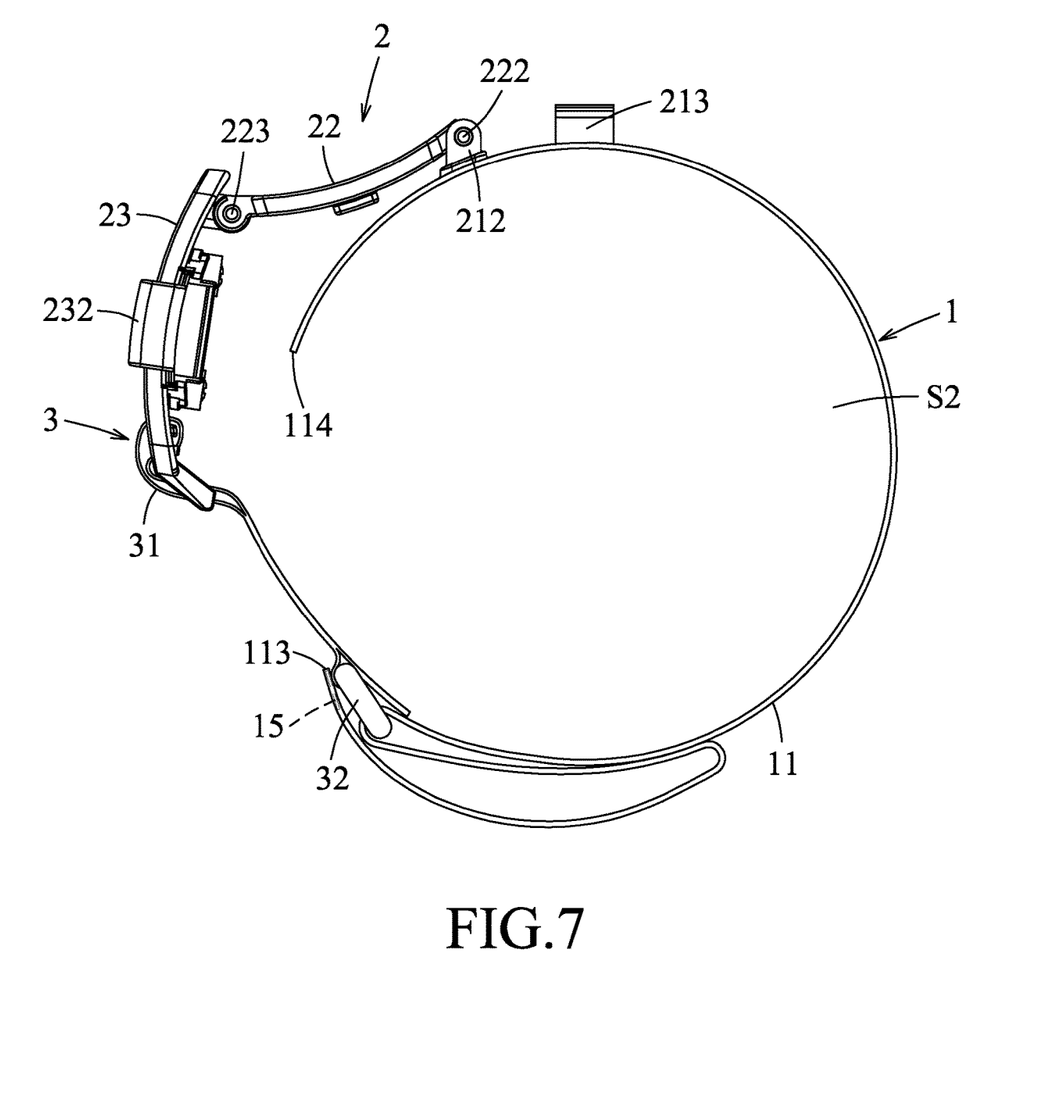
FIG. 7 is a side schematic view of the embodiment forming a second constrained space.

The connecting ring 32 is a magnetic metal ring. The first end section 113 of the cuff body 11 is operable to extend through the connecting ring 32 and be folded back to attach at least one of the fastening portions 13 to the first fastening portion 12 so as to form a first constrain space (S1) (as shown in FIG. 6) with the band cuff 1, the linking unit 2 and the connecting unit 3 when the operating mechanism 23 is in the fixed state, and to form a second constrain space (S2) (as shown in FIG. 7) with the band cuff 1, the linking unit 2 and the connecting unit 3 when the operating mechanism 23 is in the unfolded state. The second constrained space (S2) is larger than the first constrained space (S1).

In first use, the cuff 1 can be operated by other aids of the wearer around an arm of the wearer and to set the first constrained space (S1) to an appropriate size.

Afterwards, the wearer can put on and take off the arm band accessory by putting the operating mechanism 23 in the unfolded state. That is, when the operating mechanism 23 is in the unfolded state the second constrained space (S2) is formed and is greater than the first constrained space (S1) so that sufficient space for the wearer's arm to move relative to the arm band accessory and is convenient to put on or take off the arm band accessory.

When the wearer desires to measure the blood pressure, the operating mechanism 23 is first moved to the unfolded state in order to pass the arm through the arm band accessory, then after the arm band accessory is at an appropriate position, the operating mechanism 23 is moved to the fixed state to return to the first constrained space (S1) for measurement of the blood pressure and obtain a more accurate measurement value.

In this embodiment, the length of the cuff body 11 is suitable for a range of arm circumference sizes ranging from 9 to 17 inches, so that groups with small arm circumferences to large arm circumferences are covered.

When used by the groups with small arm circumference, the second fastening portion 13 that is closer to the second end section 114 is fastened to the first fastening portion 12, and the second fastening portion 13 that is closer to the first end section 113 is not fastened to the first fastening portion 12, at this point the cuff body 11 can be folded again, and the first end section 113 of the cuff body 11 is magnetically attracted to the connecting ring 32 by the magnet member 15 such that the first end section 113 of the cuff body 11 is not hanging loose. In a variation of the embodiment, only one second fastening portion 13 may also be implemented.

In summary, by virtue of the linking unit 2, the first constrained space (S1) can be formed on the arm band accessory for measurement of the blood pressure, or the arm band accessory forms the second constrained space (S2) to put on and take off the arm band accessory, facilitating one hand operation by the wearer.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. An arm band accessory, comprising:
a band cuff including a cuff body that extends in a longitudinal direction, a first fastening portion, and at least one second fastening portion, said cuff body having a first surface and a second surface that are opposite to each other, and a first end section and a second end section that are opposite to each other in said longitudinal direction, two ends of each of said first surface and said second surface being respectively located at said first end section and said second end section of said cuff body, said first fastening portion and said at least one second fastening portion being disposed on said first surface, said at least one second fastening portion operable to be detachably fastened to said first fastening portion;
a linking unit including a securing member, a rotatable member, and an operating mechanism, said securing member being mounted to said cuff body and proximate to said second end section, said rotatable member being pivotally connected to said securing member and said operating mechanism, said operating mechanism being operable to convert between a fixed state, where said operating mechanism is stacked on said rotatable member and is detachably fixed to said securing member, and an unfolded state, where said operating mechanism is away from said securing member and where said operating mechanism and said rotatable member are unfolded; and
a connecting unit including a connecting belt and a connecting ring, said connecting belt having opposite ends that are respectively connected to said operating mechanism and said connecting ring, said first end section being operable to extend through said connecting ring and be folded back so as to attach said at least one second fastening portion to said first fastening portion to form a first constrained space with said band cuff, said linking unit and said connecting unit when said operating mechanism is in said fixed state, and to form a second constrained space with said band cuff, said linking unit and said connecting unit when said operating mechanism is in said unfolded state, said second constrained space being larger than said first constrained space;
wherein said band cuff further includes an inflatable bladder disposed inside said cuff body and in proximity to said second end section, and
wherein said securing member has a base body that is bent and flexibly expandable, and that is partially overlapped with said inflatable bladder.

2. The arm band accessory as claimed in claim 1, wherein said base body is disposed in said cuff body, and said securing member further has a first pivot portion connected to said base body and protruding out of said first surface for connection with said rotatable member, and an engaging portion connected to said base body and protruding out of said first surface for engagement with said operating mechanism, said engaging portion being farther away from said second end section than said first pivot portion.

3. The arm band accessory as claimed in claim 2, wherein said engaging portion has two engaging hooks spaced apart from each other in a width direction perpendicular to said longitudinal direction, said operating mechanism including a main member, two pressing members and two resilient members, said main member being connected between said rotatable member and said connecting belt, said pressing members being arranged on said main member in said width direction and being movable between a fastening position, where said pressing members are respectively engaged with said engaging hooks, and a releasing position, where said pressing members are respectively disengaged from said engaging hooks, said resilient members being respectively disposed corresponding to said pressing members to provide a restoring force for restoring said pressing members to said fastening position.

4. The arm band accessory as claimed in claim 3, wherein:
said operating mechanism further includes two limit members that are mounted to an inner surface of said main member which faces said cuff body, that are respectively disposed corresponding to said pressing members, and that cooperate with said main member to hold said pressing members;
said main member has two first edges that are parallel to said longitudinal direction and that are opposite to each other;
said pressing members are respectively located at said first edges and are movable parallel to said width direction;
said pressing members are moved toward each other when moved from said fastening position to said releasing position; and
each of said resilient members is located between the respective one of said pressing members and a respective one of said limit members.

5. The arm band accessory as claimed in claim 4, wherein:
said main member further has two limit notches recessed inwardly and respectively from said first edges and parallel to said width direction;
said limit notches correspond respectively in position to said pressing members;
each of said limit members has a securing portion fixed to said main member, two arm portions extending from said securing portion and parallel to said width direction, and two stop blocks located on ends of said arm portions respectively;
said arm portions and said securing portion cooperatively define a guide groove;
each of said pressing members has
a support portion abutting against said inner surface of said main member,
a press portion extending from said support portion, being U-shaped, and accommodating a respective one of said first edges,
a limit block connected to said press portion and slidable parallel to said width direction within a respective one of said limit notches,
an engaging segment extending from said support portion away from said main member for engaging with the respective one of said engaging hooks, and
two guide blocks extending respectively from two opposite sides of said support portion parallel to said longitudinal direction;

wherein said guide blocks abut respectively against said arm portions and are slidable parallel to said width direction within said guide groove; and wherein, when said pressing members are at said fastening position, said guide blocks of each pressing member are respectively stopped by said stop blocks of the respective one of said limit members so as to prevent separation of said pressing member from said main member.

6. The arm band accessory as claimed in claim 5, wherein:

each of said limit members further has a first positioning protrusion extending from said securing portion parallel to said width direction and located between said arm portions;

each of said pressing members further has a second positioning protrusion extending from said engaging segment parallel to said width direction toward said first positioning protrusion of the respective one of said limit members; and each of said resilient members is a compression spring, and has two ends respectively sleeved on said first positioning protrusion of the respective one of said limit members and said second positioning protrusion of the respective one of said pressing members and respectively abutting against said securing portion of the respective one of said limit members and said engaging segment of the respective one of said pressing members.

7. The arm band accessory as claimed in claim 3, wherein said rotatable member has a main body, a first pivot rod that is connected to an end of said main body, that extends in said width direction and that is pivotally connected to said first pivot portion, and a second pivot rod that is connected to another end of said main body opposite to said first pivot rod and that is pivotally connected to said main member, said main body having two openings permitting said engaging hooks to respectively pass therethrough.

8. The arm band accessory as claimed in claim 7, wherein said main member has two first edges that are parallel to said longitudinal direction and that are opposite to each other, a second edge and a third edge that are parallel to said width direction and that are connected to said first edges, a second pivot portion that is proximate to said second edge and that is pivotally connected to said second pivot rod, and a connecting portion that is proximate to said third edge and that is connected to said connecting belt, said third edge being adjacent to said first pivot rod when said operating mechanism is in said fixed state.

9. The arm band accessory as claimed in claim 1, wherein said band cuff further includes a magnet member disposed on said cuff body and adjacent to said first end section for being magnetically attracted to said connecting ring.

* * * * *